US007738954B1

(12) United States Patent  (10) Patent No.: US 7,738,954 B1
Kroll et al.  (45) Date of Patent:  Jun. 15, 2010

(54) HIS BUNDLE CONTROL

(75) Inventors: Mark W. Kroll, Simi Valley, CA (US); Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 950 days.

(21) Appl. No.: 10/830,849

(22) Filed: Apr. 22, 2004

(51) Int. Cl.
    *A61N 1/368* (2006.01)
(52) U.S. Cl. .......................................... 607/9
(58) Field of Classification Search ............... 607/4, 607/5, 9, 14
    See application file for complete search history.

(56) References Cited

U.S. PATENT DOCUMENTS

| 4,712,555 A | 12/1987 | Thornander et al. ... 128/419 PG |
| 4,788,980 A | 12/1988 | Mann et al. ........... 128/419 PG |
| 4,940,052 A | 7/1990 | Mann et al. ........... 128/419 PG |
| 4,944,298 A | 7/1990 | Sholder ................ 128/419 PG |
| 5,466,254 A | 11/1995 | Helland ....................... 607/123 |
| 5,683,447 A | 11/1997 | Bush et al. .................. 607/126 |
| 5,876,422 A | 3/1999 | van Groeningen ............. 607/3 |
| 6,314,323 B1 | 11/2001 | Ekwall ........................ 607/23 |
| 6,609,027 B2 | 8/2003 | Kroll et al. ...................... 607/9 |
| 6,718,206 B2* | 4/2004 | Casavant ....................... 607/9 |
| 7,096,064 B2* | 8/2006 | Deno et al. .................... 607/9 |
| 2002/0120318 A1* | 8/2002 | Kroll et al. .................. 607/149 |

OTHER PUBLICATIONS

Rattay, Frank, "Electrical Nerve Stimulation," Electrical Nerve Stimulation: Theory, Experiments and Applications. 1990, page number unknown.

* cited by examiner

*Primary Examiner*—Carl H Layno
*Assistant Examiner*—Rex Holmes

(57) ABSTRACT

An exemplary controller includes an input for receiving information related to a signal of supraventricular origin, control logic to determine a control signal and an output to deliver the control signal to thereby actively filter the signal of supraventricular origin in the His bundle. Other exemplary methods, devices, systems, etc., are also disclosed.

27 Claims, 9 Drawing Sheets

EXEMPLARY ANATOMICAL DIAGRAM

EXEMPLARY ANATOMICAL DIAGRAM

EXEMPLARY CONTROL SYSTEM

HIS BUNDLE CONTROL

TECHNICAL FIELD

Subject matter presented herein generally relates to treatment of cardiac conditions via His bundle control.

BACKGROUND

In a normal human heart, the sinus node, located generally near the junction of the superior vena cava and the right atrium, acts as the primary natural pacemaker. For a variety of reasons, cardiac rhythm may be compromised if the sinus node malfunctions or its pacemaker activity is supplanted by other activity. For example, a change in autonomic tone can accelerate (e.g., increase in sympathetic activity or decrease in parasympathetic activity) or decelerate (e.g., increase in parasympathetic activity or decrease in sympathetic activity) the sinus node's pacing rate. Further, the presence of an atrial arrhythmia generally indicates that sinus node pacing has been supplanted or become ineffective. In these examples, consequences for one or both atria are apparent; however, profound consequences can also exist for ventricular activity.

In a normal human heart, the atrio-ventricular conduction system provides for coordination between atrial and ventricular activity; however, as discussed above, if the atrial activity is compromised, then a high likelihood exists that ventricular activity will be compromised. In general, the atrio-ventricular conduction system has few inherent mechanisms to prevent inappropriate atrial activity from affecting ventricular activity. The mechanisms that do exist include secondary pacemaker activity and low pass filtering such as 2:1 atrio-ventricular node block, both of which can be affected by or responsive to autonomic activity. To augment or replace these natural mechanisms various artificial mechanisms have been proposed to maintain proper ventricular activity where inappropriate atrial activity exists. Such artificial mechanisms include ablation of the atrio-ventricular node in conjunction with artificial ventricular pacing. Other artificial mechanisms involve direct stimulation of the atrio-ventricular node or parasympathetic nerves to achieve some degree of reversible atrio-ventricular node block. Overall, such mechanisms should consider the complex physiology of the atrio-ventricular node, which can vary considerably from patient to patient.

To overcome various issues associated with artificial control of the atrio-ventricular, mechanisms described herein focus on the His bundle. The His bundle has sparse autonomic innervation and a narrow tubular histology consisting of Purkinje fibers in longitudinal compartments. Various exemplary mechanisms presented herein account for such features and allow for control of conduction through the His bundle.

SUMMARY

An exemplary controller includes an input for receiving information related to a signal of supraventricular origin, control logic to determine a control signal and an output to deliver the control signal to thereby actively filter the signal of supraventricular origin in the His bundle. Other exemplary methods, devices, systems, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims.

Overview

Various mechanisms for artificial control of the His bundle are presented herein. Some mechanisms may act to block or filter supraventricular activity that could be detrimental to proper ventricular function. In addition, stimulation, pacing or anti-arrhythmia therapy may be administered to ensure or to attain beneficial cardiac performance.

An exemplary stimulation device is described below followed by a discussion of conduction dynamics and various exemplary mechanisms that aim to control conduction of the His bundle. In general, energy delivery via one or more electrodes is used to control conduction of the His bundle. Such electrodes or other electrodes or sensors may provide input to a His bundle controller.

Exemplary Stimulation Device

The techniques described below are intended to be implemented in connection with any stimulation device that is configured or configurable to stimulate nerves, stimulate muscle tissue and/or stimulate and/or shock a patient's heart (e.g., myocardial muscle tissue, etc.).

Figure 1:
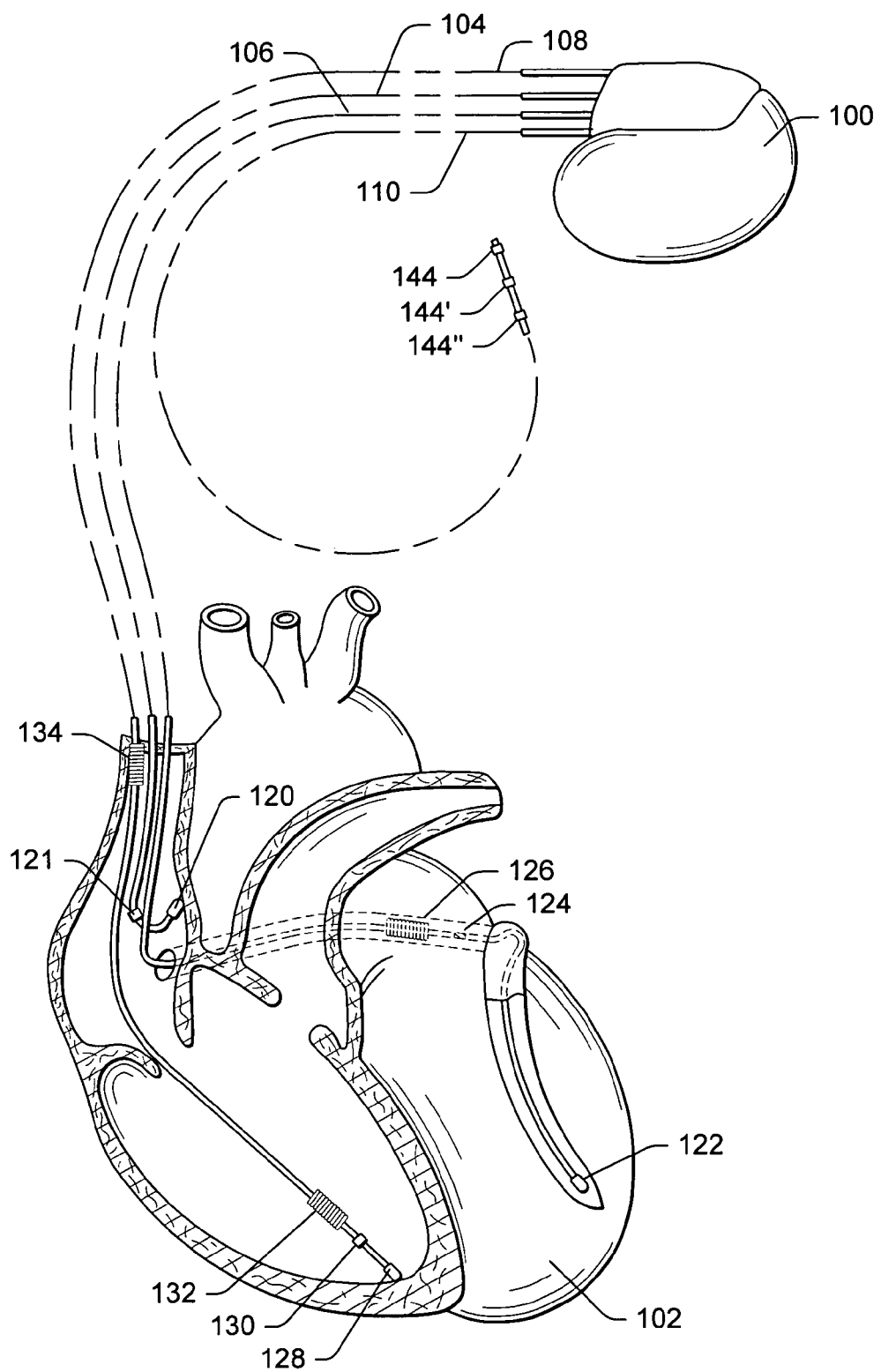
FIG. 1 is a simplified diagram illustrating an exemplary implantable stimulation device in electrical communication with at least three leads implanted into a patient's heart and optionally at least one other lead. Exemplary devices may have lesser leads as well.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of energy pulses to nerves (e.g., autonomic nerves, etc.) and/or cardiac tissue (e.g., His bundle, etc.). Such leads may alternatively or in addition to sense activity of nerves and/or cardiac tissue. The device 100 also includes a fourth lead 110 having, in this implementation, three electrodes 144, 144', 144'' suitable for delivering energy to nerves (e.g., autonomic nerves, etc.) and/or cardiac tissue (e.g., His bundle) and/or sensing physiologic signals that may be used by the implanted system to modify therapeutic parameters. The lead 110 may be positioned in and/or near a patient's heart, near a nerve (e.g., an autonomic nerve, etc.) or near other tissue within a patient's body and optionally remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for delivery of energy to nerves and/or cardiac tissue.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 may be configured to sense activity from one or more positions in or on the heart. The coronary sinus lead 106 further optionally includes electrodes for delivery of energy to autonomic nerves, other nerves and/or tissue. Such a lead may include cardiac pacing, nerve and/or muscle energy delivery functionality and may further include bifurcations or legs. For example, an exemplary coronary sinus lead includes pacing electrodes capable of delivering pacing pulses to a patient's left ventricle and at least one electrode capable of delivering energy to a nerve (e.g., autonomic nerve, etc.) and/or other tissue (e.g., His bundle).

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of delivering energy to a nerve and/or other tissue; such an electrode may be positioned on the lead or a bifurcation or leg of the lead. For example, an exemplary right ventricular lead includes pacing electrodes capable of delivering pacing pulses to a patient's right ventricle and at least one electrode capable of delivering energy to a nerve (e.g., autonomic nerve, etc.) and/or other tissue (e.g., His bundle).

Figure 2:
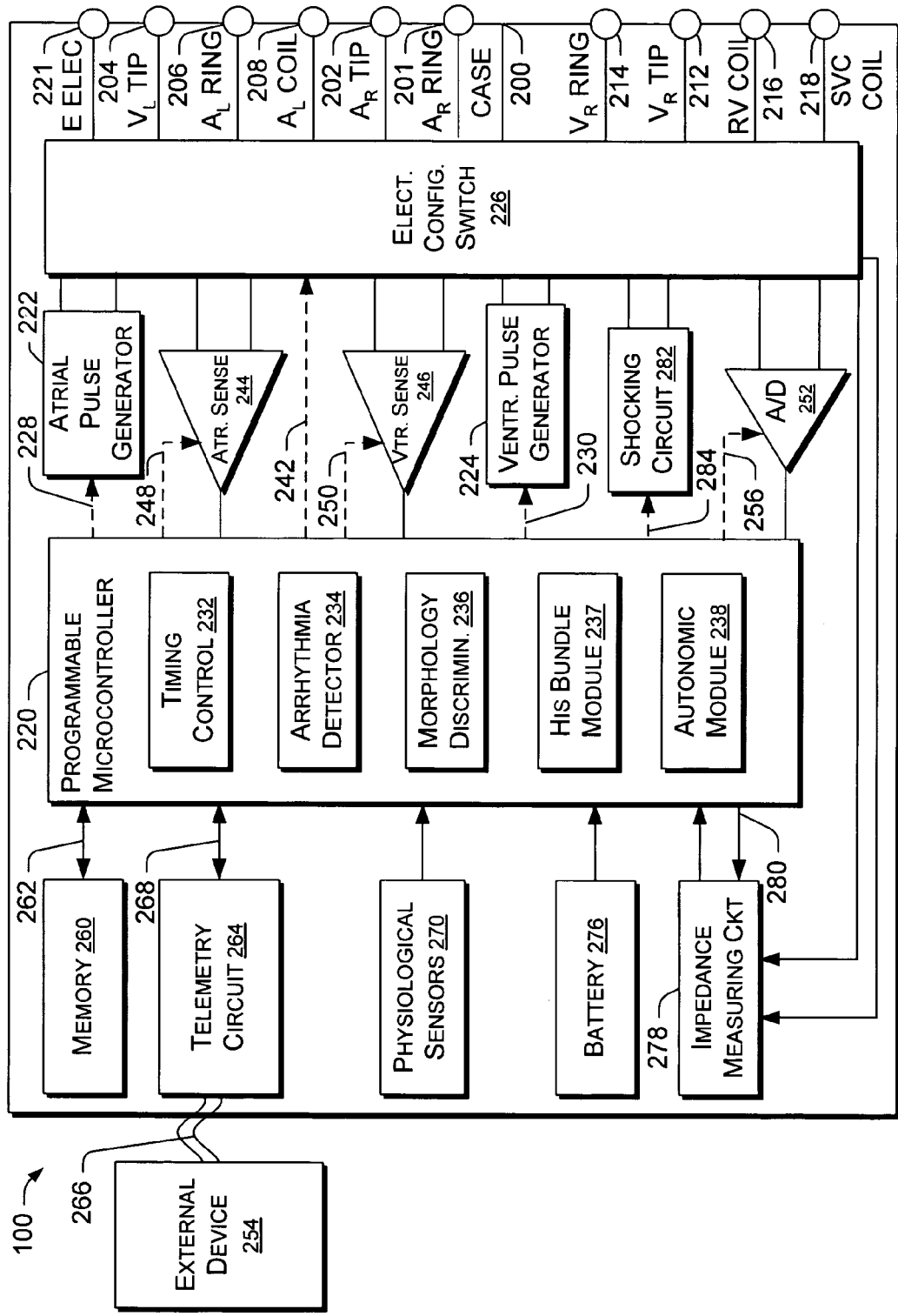
FIG. 2 is a functional block diagram of an exemplary implantable stimulation device illustrating basic elements that are configured to provide cardioversion, defibrillation, pacing stimulation, His bundle control, etc.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering energy to nerves (e.g., autonomic nerves, etc.) and/or tissues (e.g., His bundle, etc.). While a particular multi-chamber device is shown, it is to be appreciated and understood that this is done for illustration purposes only. Thus, the techniques and methods described below can be implemented in connection with any suitably configured or configurable stimulation/energy delivery device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or energy delivery therapies.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or energy delivery to tissue, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or energy delivery to tissue, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable energy delivery electrodes is also possible via these and/or other terminals (e.g., via an energy delivery terminal E ELEC 221).

To support right chamber sensing, pacing, shocking, and/or energy delivery to tissue, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable energy delivery and/or sensing electrodes is also possible via these and/or other terminals (e.g., via the energy delivery terminal E ELEC 221).

At the core of the stimulation device 100 is a programmable microcontroller 220 that controls the various modes of stimulation therapy and/or energy delivery therapy. As is well known in the art, microcontroller 220 typically includes a microprocessor, or equivalent control circuitry, designed specifically for controlling the delivery of stimulation therapy and/or energy delivery therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or energy delivery to tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation or energy delivery pulses.

Microcontroller 220 further includes timing control circuitry 232 to control the timing of the stimulation or energy delivery pulses (e.g., pacing rate, atrio-ventricular (AV) delay, interatrial conduction (A-A) delay, or interventricular conduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes, for example, an arrhythmia detector 234, a morphology discrimination module 236, His bundle module 237, and an autonomic module 238. These components can be utilized by the stimulation device 100 for determining desirable times to administer various therapies. The aforementioned components may be implemented in hardware as part of the microcontroller 220, or as software/firmware instructions programmed into the device and executed on the microcontroller 220 during certain modes of operation. Various exemplary methods described herein are optionally implemented as logic, which may be embodied in software and/or hardware.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation or energy pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, a clinician may program the sensing polarity independent of the stimulation polarity. The sensing circuits (e.g., 244 and 246) are optionally capable of obtaining information indicative of tissue capture. The sensing circuits 244, 246, via switches, etc., may also be used to sense information related to His bundle activity and/or control.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation and/or other low level signals.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. Other features for arrhythmia detection, confirmation, etc. are discussed below and may be suitable as appropriate. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Nerve, muscle and/or cardiac signals (e.g., His bundle, etc.) are also optionally applied to inputs of an analog-to-digital (ND) data acquisition system 252. The data acquisition system 252 is, for example, configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or a His bundle lead (e.g., lead 110, etc.) through the switch 226 to sample signals across any of desired electrode (e.g., unipolar) or electrodes (e.g., multipolar).

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. The exemplary device 100 may include an ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include one or more physiologic sensors 270. For example, a physiologic sensor commonly referred to as a "rate-responsive" sensor is optionally included and used to adjust pacing stimulation rate according to the exercise state of the patient. However, one or more of the physiologic sensors 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, diurnal changes in activity (e.g., detecting sleep and wake states), etc. Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the one or more physiologic sensors 270 may also be external to the stimulation device 100, yet still be implanted within or carried by the patient.

In particular, the one or more physiologic sensors 270 optionally include a position and/or movement sensor mounted within the housing 200 of the stimulation device 100 to detect movement in the patient's position or the patient's position. Such a sensor may operate in conjunction with a position and/or movement analysis module (e.g., executable in conjunction with the microcontroller 220). The position and/or movement sensor may be implemented in many ways. In one particular implementation, the position sensor is implemented as an accelerometer-based sensor capable of measuring acceleration, position, etc. For example, such a sensor may be capable of measuring dynamic acceleration and/or static acceleration. In general, movement of the patient will result in a signal from the accelerometer. For example, such an accelerometer-based sensor can provide a signal to the microcontroller 220 that can be processed to indicate that the patient is undergoing heightened physical exertion, moving directionally upwards or downwards, etc.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgment occurs; measuring respiration rate and/or tidal volume; measuring thoracic or other impedances for determining shock or other thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

As already mentioned, the device 100 of FIGS. 1 and 2 has features suitable to call for and/or deliver energy to tissue to control the His bundle. With respect to calling for energy delivery to the His bundle, the His bundle module 237 may be used and with respect to delivery, any of the various pulse generators, electrodes, etc., may be used.

Figure 3:
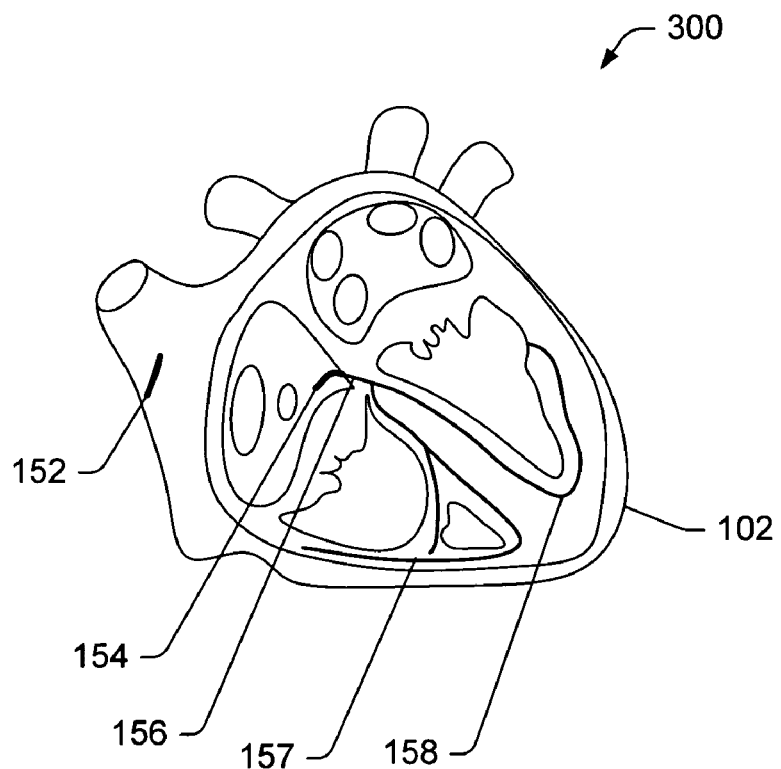
FIG. 3 is a cross-sectional anatomical diagram of a heart illustrating various components of the atrio-ventricular conduction system.

FIG. 3 shows an approximate cross-sectional anatomical diagram 300 of a human heart 102. The diagram 300 exhibits various components of the atrio-ventricular conduction systems including the sin θ-atrial node (SA node) 152, the atrio-ventricular node (AV node) 154, the His bundle 156, a right bundle branch 157 and a left bundle branch 158. The His bundle 156 penetrates the right fibrous trigone and then divides into the right bundle branch 157 and the left bundle branch 158. Thus, a lead or an electrode may access the right atrium of the heart 102 via the superior vena cava and be secured or otherwise fixed proximate to the His bundle 156. Various exemplary mechanism discussed herein include use of such a lead or an electrode to achieve His bundle control. Such control may rely on sensing as well as delivery of energy to the His bundle.

His bundle sensing is discussed in U.S. Pat. No. 6,609,027, to Kroll et al., which is incorporated herein by reference. Various electrodes, leads, devices, etc., disclosed in the 6,609,027 patent may be used to achieve sensing and/or other features suitable for His bundle control. His bundle stimulation for ventricular activation is discussed in a study by Deshmukh et al., "Permanent, Direct His-Bundle Pacing—A Novel Approach to Cardiac Pacing in Patients With Normal His-Pukinjie Activation," *Circulation:* 2000:101(8)869-877, which is incorporated herein by reference. Where His bundle control includes His bundle stimulation for ventricular activation, various leads, electrodes, etc., disclosed in the Deshmukh study may be used.

Figure 4:
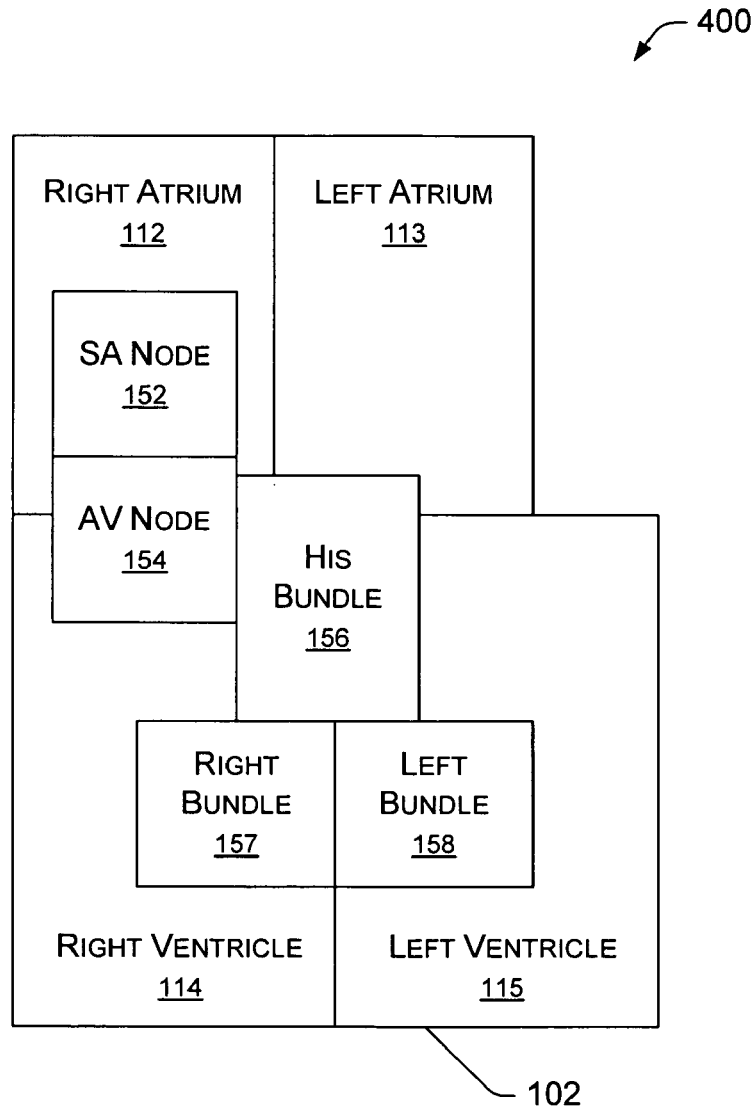
FIG. 4 is a simplified anatomical diagram of a heart and various components of the atrio-ventricular conduction system.

FIG. 4 shows an approximate block diagram 400 of the heart 102 of FIG. 3 and its corresponding atrio-ventricular conduction system. The block diagram 400 includes the right atrium 112, the left atrium 113, the right ventricle 114 and the left ventricle 115. Components of the conduction system are shown in approximate relationship to the various chambers 112, 113, 114 and 115. The SA node 152 appears in the right atrium 112, the AV node 154 appears at a boundary between the right atrium 112 and the right ventricle 114, the His bundle 156 intersects the atria 112, 113 and the ventricles 114, 115 while the right bundle 157 appears in the right ventricle 114 and the left bundle appears in the left ventricle 115.

Figure 5:
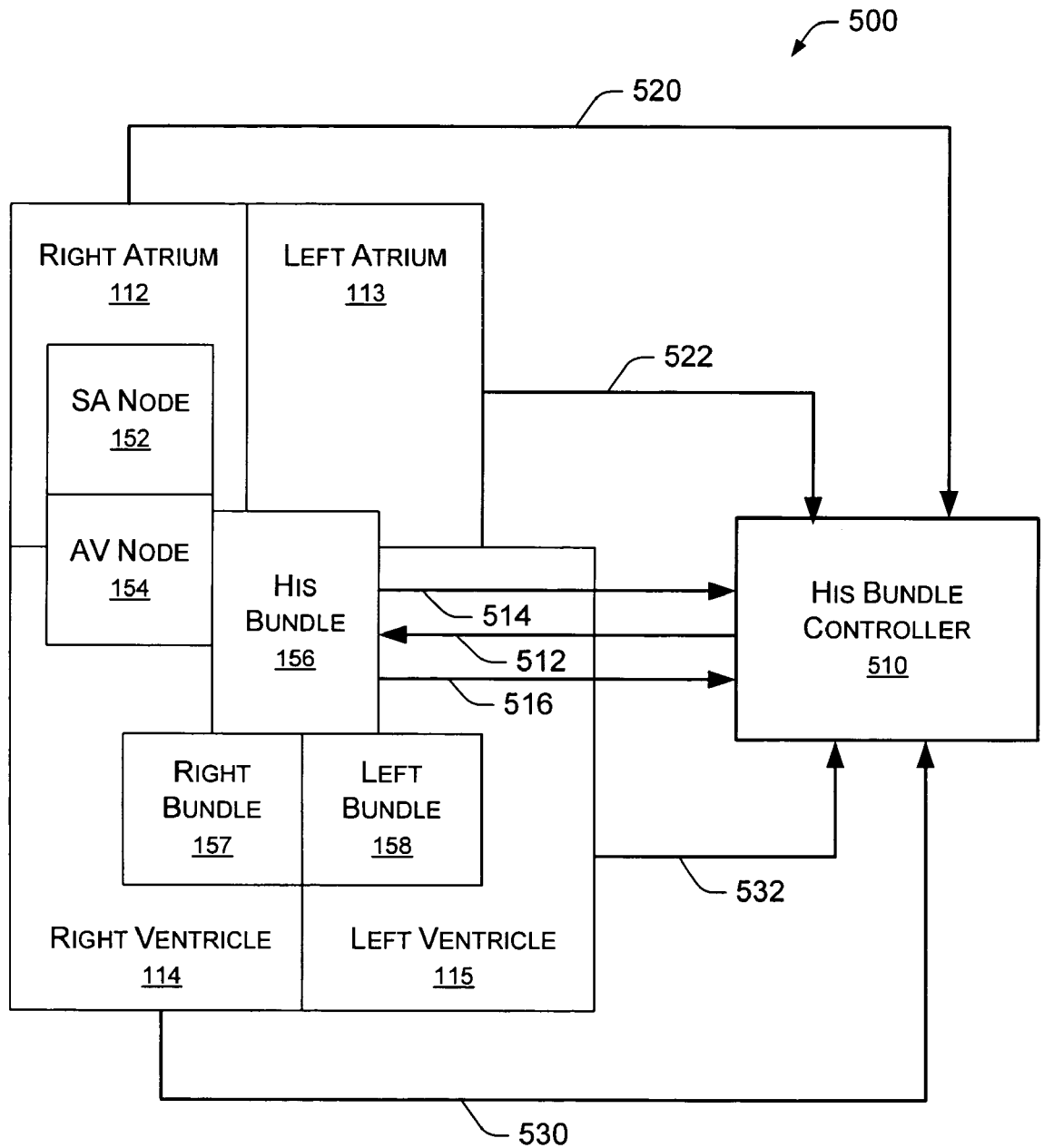
FIG. 5 is a schematic of an exemplary control system that includes a His bundle controller.

FIG. 5 shows an exemplary control system 500 that includes the block diagram 400 of FIG. 4 and a His bundle controller 510. The His bundle controller 510 includes at least one output 512 for delivery of energy to the His bundle. Control of the output 512 may rely on information received from one or more inputs. For example, the controller 510 includes a pre-delivery site His bundle input 514, a post-delivery site His bundle input 516, a right atrial input 520, a left atrial input 522, a right ventricular input 530 and a left ventricular input 532. Other inputs are optional such as the physiological sensors 270 discussed above (e.g., see FIG. 2). In general, the His bundle controller 510 receives at least one input (e.g., 514, 516, 520, 522, 530, 532, etc.), determines an appropriate control energy or control signal and then delivers the energy via the output 512 to affect or control the His bundle. The appropriate control energy may rely on one or more parameters such as frequency, amplitude, timing, etc. Control logic may determine such parameters based at least in part on one or more inputs. An exemplary controller may rely on control logic aimed at filtering supraventricular signals conducted by the His bundle. Further, an exemplary controller may include control logic aimed at filtering supraventricular signals conducted by the His bundle and stimulating the ventricles.

Figure 6:
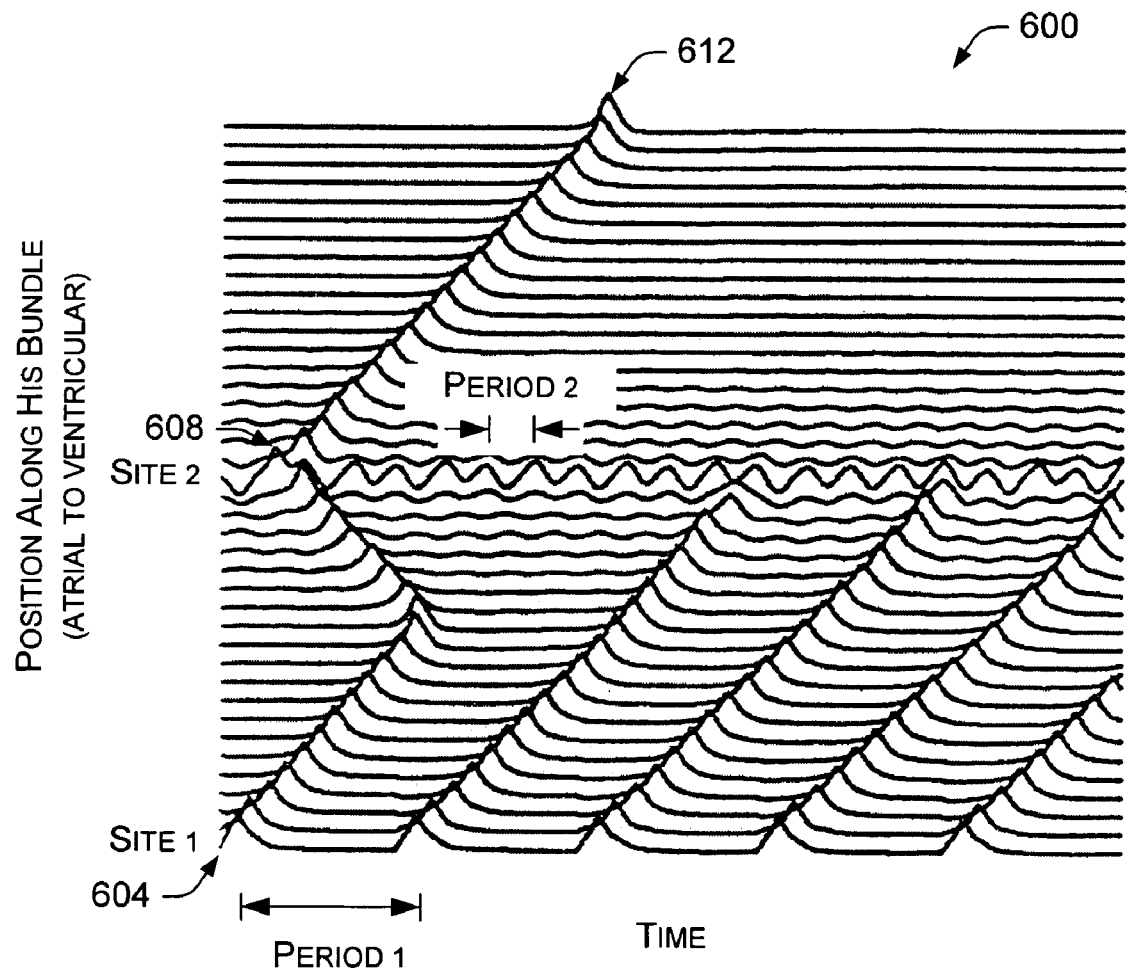
FIG. 6 is a plot that of an exemplary control scheme for filtering signals in the His bundle.

With respect to filtering, FIG. 6 shows a plot 600 for exemplary control scheme that acts to filter a high frequency supraventricular signal 604 with a control signal 608. For example, the exemplary control scheme may act to block the supraventricular signal 604. The plot 600 depicts signal amplitude versus time for a variety of positions along the His bundle from atrial to ventricular. At Site 1, the supraventricular signal 604 of Period 1 propagates toward Site 2. The supraventricular signal 604 may correspond to inappropriate atrial activity such as that associated with atrial fibrillation. At Site 2, a control signal 608, sinusoidal and of Period 2, is delivered to affect the supraventricular signal 604 (e.g., to cancel, diminish, filter, etc.). In this example, the control signal 608 is delivered to actively filter the supraventricular signal 604 and, in particular, to act as a blocking filter or a low pass filter. Period 2 of the control signal 608 is approximately 25% of Period 1 of the supraventricular signal 604 and hence, via wave theory, acts to block the supraventricular signal 604. In the exemplary scheme 600, a control artifact 612 remains that propagates along the His bundle. Depending on the amplitude, frequency, timing, etc., of the control signal 612, the artifact 612 may be of no significant consequence. For example, if the control signal 608 is switched in a manner such that the artifact 612 reaches the ventricles during a physiological refractory period, then the artifact may be expected to have no significant effect on the ventricles.

The wave theory used in the exemplary control scheme 600 has been applied to nerve transmission and discussed in the text Electrical Nerve Stimulation (Rattay, Frank. 1990. *Electrical Nerve Stimulation: Theory, Experiments and Applications*. Wien: Springer-Verlag), which is incorporated by reference herein. While the His bundle is not a nerve, the overall structure of the His bundle acts as a transmission conduit or a set of parallel conduits that conduct signals in a manner analogous to that of a nerve. Hence, wave theory can be applied to control conduction of signals via the His bundle. Control may include various types of filtering as appropriate such as low pass, blocking, etc. While various examples are directed to His bundle control, other exemplary methods, devices, systems, etc., may include an input for receiving information related to a nerve signal, control logic to determine a control signal and an output to deliver the control signal to thereby actively filter the nerve signal.

Figure 7:
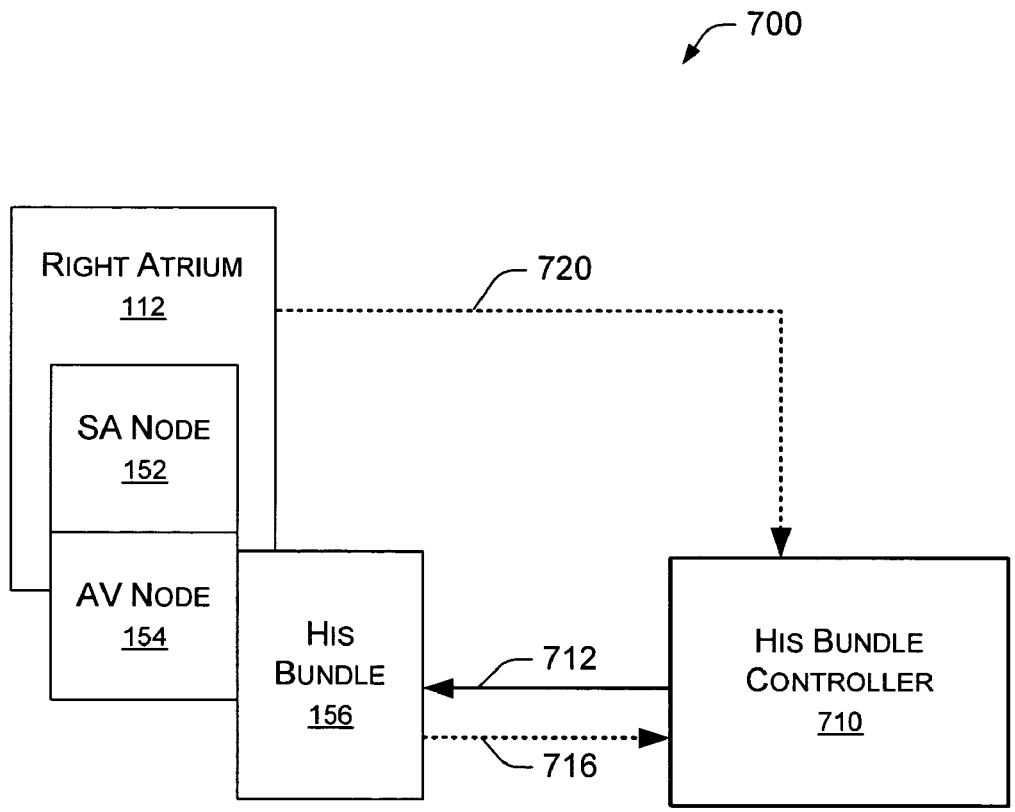
FIG. 7 is a schematic of an exemplary control system that includes a His bundle controller.

FIG. 7 shows an exemplary control system 700 that includes various features of the control system 500 of FIG. 5. The control system 700 includes a His bundle controller 710 that has an output 712 and a right atrial input 720 and a post-delivery site input 716. In this example, the right atrial input 720 allows for detection of atrial tachycardia, atrial fibrillation, etc. In response to detection of such an atrial or supraventricular condition, the controller 710 calls for appropriate His bundle control therapy. For example, the controller 710 may detect a supraventricular signal frequency associated with the atrial condition and then determine one or more appropriate control signal parameters (e.g., frequency, amplitude, etc.). The controller 710 may then call for delivery of the control signal to affect the His bundle and output such a signal via the output 712. A feedback signal may be received by the controller 710 via the input 716 to determine if the control signal has effectively filtered the supraventricular signal. Such a feedback signal may be used to adjust the control signal as appropriate.

In another example, an exemplary control system relies on a post-delivery site input to detect inappropriate supraventricular activity. In yet another example, an exemplary control system relies on a post-delivery site input to detect inappropriate supraventricular activity and to provide feedback for adjustment of a control signal. In these various examples inappropriate supraventricular activity may be associated with inappropriate rates (e.g., too fast) or with activity that compromises ventricular activity. Various exemplary control systems for His bundle control may aim to filter "normal" supraventricular activity in a manner that allows for extension of effective atrial to ventricular contraction intervals (e.g., 2:1 atrial to ventricular contraction ratio or other ratios).

Figure 8:
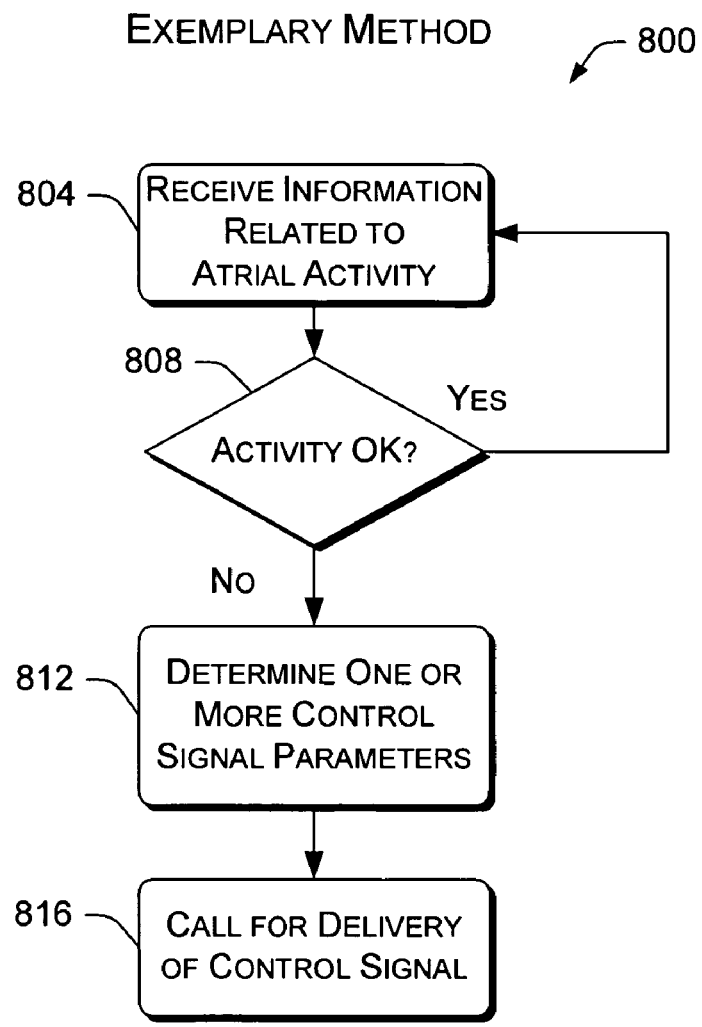
FIG. 8 is a block diagram of an exemplary method for monitoring respiratory activity and determining when an upper airway collapse may occur for giving timings and/or stimulation energies.

FIG. 8 shows a block diagram of an exemplary method 800 for His bundle control. A reception block 804 receives information related to atrial activity. For example, a right ventricular lead having one or more electrodes positioned in the right ventricle may sense atrial activity and provide such information to an implantable device (e.g., the device 100 of FIGS. 1 and 2) or controller (e.g., the controller 510 of FIG. 5). A decision block 808 follows which may rely on control logic to decide if the atrial activity is appropriate or inappropriate. For example, inappropriate atrial activity may include atrial arrhythmic activity. Such a decision may rely on an arrhythmia detector (e.g., the arrhythmia detector 234 of FIG. 2). According to the exemplary method 800, if the atrial activity is appropriate, then the method may continue at the reception block 804; however, if the atrial activity is inappropriate, then the method continues at a determination block 812. The determination block 812 determines one or more control signal parameters that aim to filter a signal associated with the inappropriate atrial activity, which if not addressed may have a detrimental affect on ventricular activity. An implantable microcontroller that optionally relies on software may be used to make such determinations (e.g., the His bundle module 237 of FIG. 2). After determination of such control signal parameters, the method 800 enters a call block 816 which calls for delivery of a control signal according to the one or more parameters. An implantable microcontroller may be used to call for such delivery (e.g., the microcontroller 220 of FIG. 2). While the exemplary method 800 refers to atrial activity, supraventricular activity may be substituted where appropriate.

Figure 9:
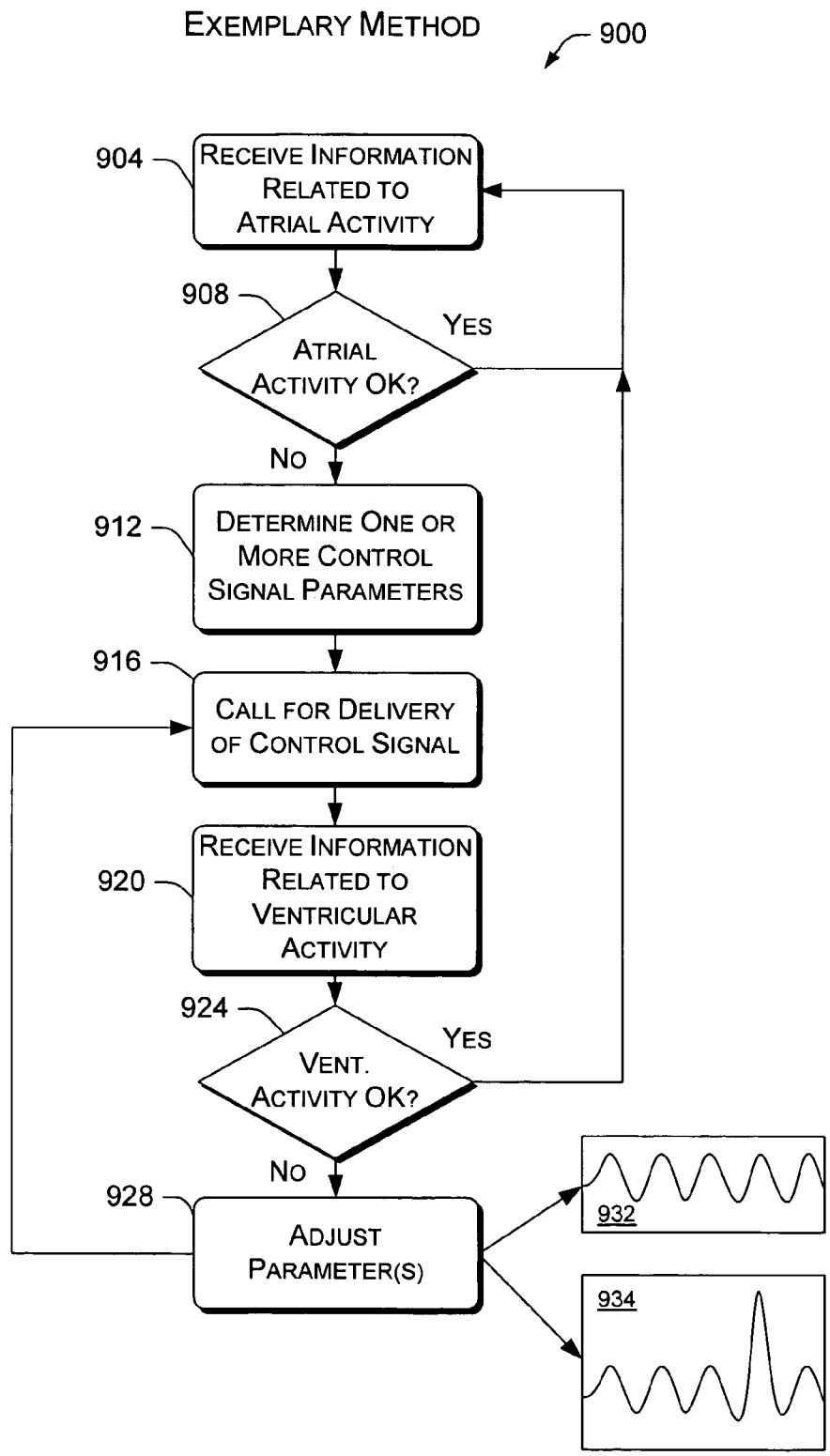
FIG. 9 is a block diagram of an exemplary method for His bundle control.

FIG. 9 shows a block diagram of another exemplary method 900 for His bundle control. While the method 900 includes various features of the method 800 of FIG. 8, it further includes blocks that pertain to ventricular information. A reception block 904 receives information related to atrial activity. A decision block 908 follows which may rely on control logic to decide if the atrial activity is appropriate or inappropriate. For example, inappropriate atrial activity may include atrial arrhythmic activity. If the atrial activity is appropriate, then the method 900 may continue at the reception block 904; however, if the atrial activity is inappropriate, then the method continues at a determination block 912. The determination block 912 determines one or more control signal parameters that aim to filter a signal associated with the inappropriate atrial activity, which if not addressed may have a detrimental affect on ventricular activity. After determination of such control signal parameters, the method 900 enters a call block 916 which calls for delivery of a control signal according to the one or more parameters.

After the call block 916, a reception block 920 receives information related to ventricular activity. A decision block 924 follows that decides if the ventricular activity is appropriate or inappropriate. If the ventricular activity is appropriate, then the exemplary method 900 continues at the reception block 904 for receiving information related to atrial activity. However, if the decision block 924 decides that the ventricular activity is inappropriate then an adjustment block 928 follows that adjusts one or more control signal parameters. The adjustment block 928 may make adjustments that act to filter and/or act to stimulate one or both ventricles. A control signal plot 932 presents a generic control signal that aims to filter a supraventricular signal arising from inappropriate atrial activity while another control signal plot 934 presents a generic control signal that aims to filter a supraventricular signal arising from inappropriate atrial activity and that aims to stimulate one or both ventricles. In particular, the control signal plot 934 includes a high amplitude peak of sufficient energy to capture one or both ventricles. Hence, such a control signal may reduce effects of atrial fibrillation and control ventricular activity. The control signal 934 therefore may include a first frequency signal at a first amplitude for filtering a signal of supraventricular origin and a second frequency signal at a second amplitude for stimulating one or both ventricles. The exemplary method 900 may continue at the call block 920 after the adjustment block 928 and the adjustment process may continue until a suitable ventricular function has been achieved.

CONCLUSION

Although exemplary mechanisms (e.g., implemented as or in methods, devices, systems, software, etc.) have been described in language specific to structural features and/or methodological acts, it is to be understood that the subject matter defined in the appended claims is not necessarily limited to the specific features or acts described.

What is claimed is:

1. A method comprising:
   applying a control signal to or near the HIS bundle, to filter a signal of supraventricular origin in the His bundle wherein the application of the control signal prevents the signal of supraventricular origin from stimulating the ventricles and wherein the application of the control signal is timed such that a control signal artifact arrives at the ventricles during a ventricular refractory period.

2. The method of claim 1 further comprising receiving information indicative of an atrial arrhythmia prior to the calling for delivery.

3. The method of claim 2, further comprising performing a mode switch in response to detection of the atrial arrhythmia, and calling for delivery in response to detection of the atrial arrhythmia.

4. The method of claim 1 further comprising delivering the control signal via one or more electrodes positioned proximate to the His bundle.

5. The method of claim 1 wherein application of the control signal actively filters the signal of supraventricular origin.

6. The method of claim 1 wherein the control signal acts to low pass filter the signal of supraventricular origin.

7. The method of claim 1 wherein the control signal acts to block the signal of supraventricular origin.

8. An implantable controller comprising:
   an input for receiving information related to a signal of supraventricular origin;

control logic to determine a control signal;

a pulse generator to generate the control signal; and an output to deliver the control signal to thereby actively filter the signal of supraventricular origin in the His bundle wherein the application of the control signal prevents the signal of supraventricular origin from stimulating the ventricles and wherein the application of the control signal is timed such that a control signal artifact arrives at the ventricles during a ventricular refractory period.

9. The implantable controller of claim 8 wherein the input includes an electrode positionable in the right atrium.

10. The implantable controller of claim 8 wherein the output includes an electrode positionable proximate to the His bundle.

11. The implantable controller of claim 8 wherein the control logic determines a frequency of a control signal based at least in part on a frequency of the signal of supraventricular origin.

12. The implantable controller of claim 8 wherein the control signal has a frequency greater than the frequency of the signal of supraventricular origin.

13. The implantable controller of claim 12 wherein the control signal has a frequency that is a multiple of the frequency of the signal of supraventricular origin.

14. The implantable controller of claim 8 wherein the control signal further includes a ventricular stimulation signal.

15. The implantable controller of claim 8 wherein the control signal includes a first frequency for filtering the signal of supraventricular amplitude and a second frequency for stimulating one or both ventricles.

16. The implantable controller of claim 8 further comprising a pacemaker.

17. The implantable controller of claim 8 further comprising an implantable cardiac defibrillator.

18. The implantable controller of claim 8 wherein the input receives information from the His bundle.

19. The implantable controller of claim 18 wherein the input receives the information from a post-delivery His bundle site.

20. The implantable controller of claim 8 further comprising feedback control logic to adjust the control signal.

21. The implantable controller of claim 20 wherein the feedback control logic relies at least in part on information related to a filtered signal.

22. The implantable controller of claim 20 wherein the feedback control logic relies on information related to ventricular activity.

23. The implantable controller of claim 8 wherein the output acts to actively block the signal of supraventricular origin in the His bundle.

24. A method comprising:

delivering a control signal at or near the His bundle to prevent conduction of a supraventricular signal through the His bundle wherein the application of the control signal prevents the signal of supraventricular origin from stimulating the ventricles and wherein the application of the control signal is timed such that a control signal artifact arrives at the ventricles during a ventricular refractory period.

25. The method of claim 24 further comprising receiving information indicative of an atrial arrhythmia prior to delivering the blocking signal.

26. The method of claim 25, further comprising performing a mode switch in response to detection of the atrial arrhythmia, and delivering the blocking signal in response to detection of the atrial arrhythmia.

27. The method of claim 24 further comprising delivering the control signal via one or more electrodes positioned proximate to the His bundle.

* * * * *